United States Patent [19]

Sanfilippo et al.

[11] Patent Number: 5,665,724

[45] Date of Patent: Sep. 9, 1997

[54] SUBSTITUTED PYRIMIDINYLAMINOTHIAZOLE DERIVATIVES USEFUL AS PLATELET AGGREGATION INHIBITORS

[75] Inventors: Pauline J. Sanfilippo, Chester Springs, Pa.; Maud Urbanski, Belle Mead, N.J.

[73] Assignee: Ortho Pharmaceutical Corporation, Raritan, N.J.

[21] Appl. No.: 446,267

[22] Filed: May 22, 1995

Related U.S. Application Data

[62] Division of Ser. No. 171,804, Dec. 22, 1993, Pat. No. 5,530,000.

[51] Int. Cl.[6] .................... A61K 31/33; A61K 31/425; C07D 239/02; C07D 411/00
[52] U.S. Cl. .................. 514/256; 514/342; 514/349; 514/397; 514/422; 514/444; 544/324; 544/329; 546/187; 546/208; 546/209; 546/270.4; 548/190
[58] Field of Search .................... 544/297, 324, 544/329; 514/275, 256, 342, 349, 397, 422, 444; 546/187, 208, 209, 276, 280; 548/190

[56] References Cited

U.S. PATENT DOCUMENTS 4,791,200 12/1988 Press et al. .
5,530,000 6/1996 Sanfilippo et al. .................... 514/252

OTHER PUBLICATIONS

CA 111: 19481 (US 4818270) Apr. 4, 1989.
CA 114: 62123 (EP 384250) Aug. 29, 1990.
Chem. Pharm. Bull. 39 651–657 (1991).
Singh, et al. Indian Journal of Chemistry 1983, 22B, 37–42.
Beyer, et al. Chem. Ber. 1962, 89, 893–901.
CA 111: 96975, 1989.
CA 100: 209516, 1984.
CA 95: 25097, 1981.

*Primary Examiner*—Shean C. Wu
*Attorney, Agent, or Firm*—Kenneth J. Dow

[57] ABSTRACT

This invention relates to substituted thiazole derivatives of the following general formula, the substituent groups of which are as defined in the specification herein:

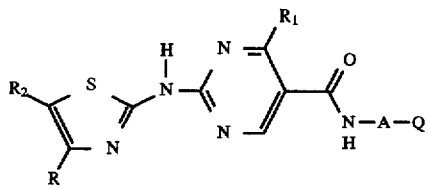

These compounds are useful as inhibitors of platelet aggregation and inhibitors of adhesion molecules and may be provided in pharmaceutical compositions and in methods of treating reperfusion thrombosis injury in patients. Also included are novel intermediates for preparing the compounds of the invention.

17 Claims, No Drawings

SUBSTITUTED PYRIMIDINYLAMINOTHIAZOLE DERIVATIVES USEFUL AS PLATELET AGGREGATION INHIBITORS This is a division of application Ser. No. 08/171,804, filed Dec. 22, 1993 now U.S. Pat. No. 5,530,000, which is hereby incorporated by reference.

FIELD OF THE INVENTION

This invention relates to substituted pyrimidinylaminothiazole derivatives as described further below. These compounds are useful as inhibitors of platelet aggregation and inhibitors of adhesion molecules and may be provided in pharmaceutical compositions and in methods of treating reperfusion thrombosis injury in patients.

BACKGROUND OF THE INVENTION

Arterial thrombosis is primarily responsible for acute myocardial infarction, unstable angina and thrombotic stroke while venous thrombosis is associated with pulmonary embolism and deep vein thrombosis. A dynamic balance exists between coagulation and fibrinolysis which are regulated by the enzymes thrombin and plasmin, respectively. Superimposed on this is the process of platelet aggregation and platelet adhesion to vessel walls. Inhibition of platelet aggregation is a means of treating thrombosis for reperfusion injury. The present invention focuses on new chemical compounds which demonstrate platelet aggregation inhibition.

The present invention provides novel pyrimidinylaminothiazole compounds which are useful as inhibitors to platelet aggregation and adhesion molecules and novel intermediate compounds for producing such inhibitor compounds. The compounds of the invention are useful for treating reperfusion thrombosis injury in patients.

Various thiazole derivatives have been identified which have biological activity. For example U.S. Pat. No. 4,791,200 discloses compounds of the formula:

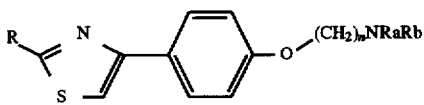

wherein R is H, alkyl, aryl or substituted phenyl and Ra and Rb are H, alkyl, aryl or substituted phenyl. These compounds are disclosed as antisecretory agents.

Chem. Pharm. Bull. 39 651–657 (1991) discloses compounds of the formula:

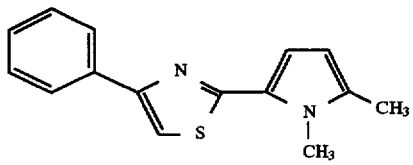

wherein diphenylimidazole and diphenyl thiazole derivatives are described as inhibitors of platelet aggregation via an arachidonic acid mechanism.

Singh, et al. *Indian Journal Of Chemistry* 1983, 22B, 37–42, disclose a series of compounds of the following formula:

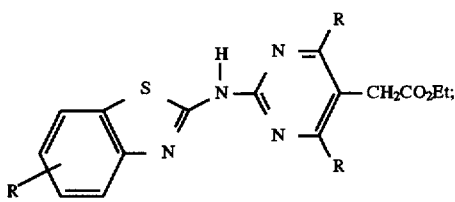

wherein R is independently selected from H, OH, Me and OMe and the compounds are described as antinflammatory agents.

Beyer, et al. Chem. Ber. 1962, 89, 893–901, disclose a series of compounds of the following formula:

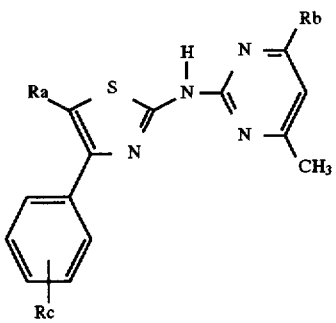

wherein Ra is selected from phenyl, methyl or hydrogen, Rb is selected from methyl or hydroxyl, Rc is selected from hydrogen, bromine or chlorine. These compounds were apparently synthesized for their synthetic challenge alone.

Although the disclosed compounds of Singh, et al. and Beyer, et al. have an pyrimidinylaminothiazole backbone, their method of synthesis and their biological activity do not disclose or suggest the compounds of the present invention.

It is therefore an object of the present invention to provide novel thiazole derivatives which are useful as platelet aggregation inhibitors and their methods of use. Additional objects and advantages of the invention will be set forth, in part, in the description which follows and in part will be obvious from this description, or may be learned by practice of the invention. The objects and advantages of the invention are realized and obtained by means of the methods, and the combinations particularly pointed out in the appended claims.

SUMMARY OF THE INVENTION

To achieve the objects in accordance with the purposes of the invention, as embodied and fully described herein the present invention relates to substituted pyrimidinylaminothiazole derivatives of the following formula:

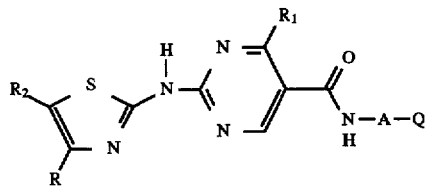

wherein

R and $R_2$ are independently selected from hydrogen, alkyl ($C_1$–$C_5$), trifluoromethyl, phenyl, or substituted phenyl, where the phenyl substituents are selected from the group consisting of cyano, nitro, trifluoromethyl, carboxy, amino, carboxamido, tosyl, bromo, chloro, iodo, fluoro, alkyl ($C_1$–$C_5$), carboalkoxy ($C_1$–$C_4$) and alkoxy ($C_1$–$C_5$);

$R_1$ is selected from the group consisting of hydrogen, alkyl ($C_1$–$C_5$), trifluoromethyl, phenyl or substituted phenyl wherein the phenyl substituents are as defined in R, substituted heterocycles such as thiophene wherein the substituents are as defined in R and $R_1$;

A is selected from the group consisting of alkyl ($C_2$–$C_9$), branched alkyl ($C_3$–$C_9$) or phenyl; and Q is selected from hydroxy, alkoxy ($C_1$–$C_5$), halogen or $NR_3R_4$, where $R_3$ and $R_4$ are independently selected from the group consisting of hydrogen, alkyl ($C_1$–$C_5$), and cycloalkyl ($C_3$–$C_8$), or $NR_3R_4$ may be taken together to form a heterocyclic ring such as piperidine, pyrrolidine, pyrrolidinone, piperidinone, phthalimide, imidazole, substituted piperazine or morpholine or $NR_3R_4$ may be a guanidine, urea, amidine, or substituted amidine wherein the substituents are selected from the group consisting of alkyl ($C_1$–$C_4$), hydroxy and amino.

The present invention also includes pharmaceutically acceptable salts of the above-described compounds.

The substituted pyrimidinylaminothiazole derivatives and their pharmaceutically acceptable salts are nonpeptidal adhesion molecule antagonists which inhibit platelet aggregation. These compounds therefore influence cell-cell and cell-matrix interactions. They inhibit the binding of fibrinogen to activated blood platelets. In particular, they prevent the formation of blood platelet thrombi and thus can be used to control or prevent illnesses such as thrombosis, stroke, unstable angina, cardiac infarct, inflammation and arteriosclerosis. The present invention thus provides for methods of treating reperfusion thrombosis injury in a patient comprising the step of administering to a patient a platelet aggregation inhibiting effective amount of a compound as described above. The present invention also provides for pharmaceutical compositions comprising one or more compounds as described above and a pharmaceutically inert carrier.

As embodied and fully described herein, the invention further comprises novel intermediate compounds for preparing the derivatives described above. These novel intermediate compounds have the formula:

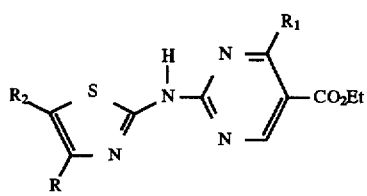

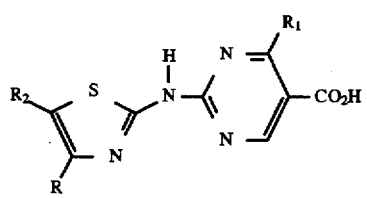

wherein R, $R_1$ and $R_2$ are as defined above.

It is to be understood that both the foregoing general description and the following detailed description are exemplary and explanatory only and are not intended to be restrictive of the invention as claimed.

DETAILED DESCRIPTION OF THE PREFERRED EMBODIMENTS OF THE INVENTION

Reference will now be made in detail to present preferred embodiments of the invention, examples of which are illustrated in the following examples section. In accordance with the invention novel compounds, compositions and methods are provided to achieve the objects in accordance with the purposes of the invention, as embodied and fully described herein.

The invention relates to substituted pyrimidinylaminothiazoles which have activity as adhesion molecule inhibitors which are useful as anticoagulants or anti-inflammatory agents. Several of the intermediates used in the synthesis of the target molecules are novel compounds and are considered to be part of the invention.

The substituted pyrimidinylaminothiazoles of the invention are prepared as outlined in the following scheme:

SCHEME I

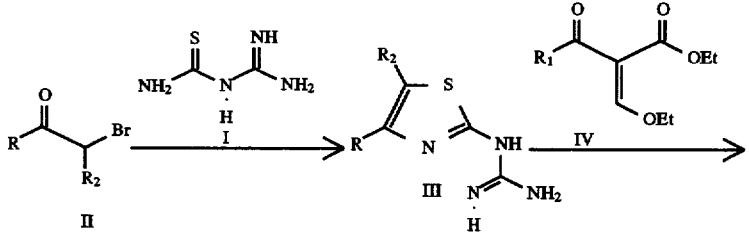

-continued
SCHEME I

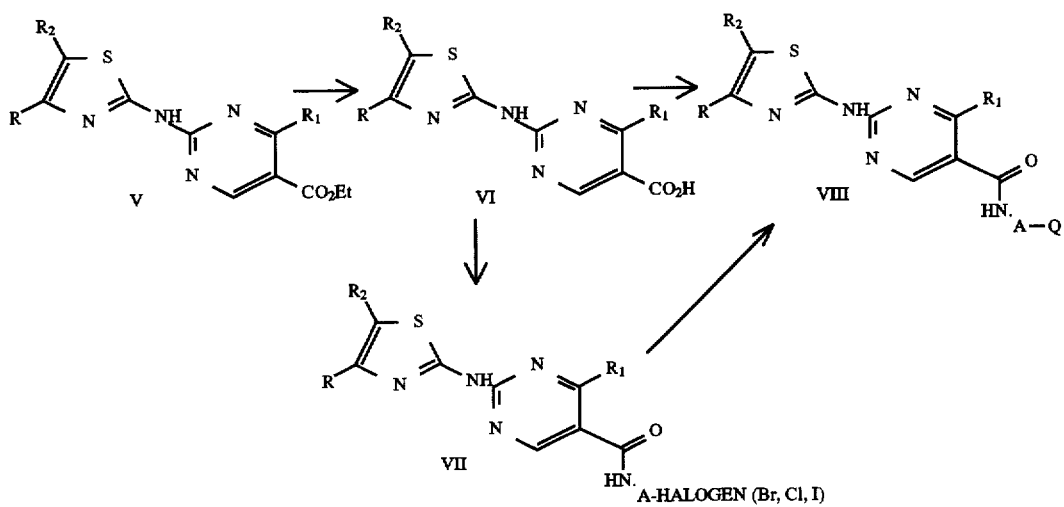

As can be seen from Scheme 1, treatment of N-amidinothiourea with an appropriately substituted alpha-haloketone in an alcoholic solvent such as ethanol for 3–12 hours (h) gives the guanidinothiazole derivative III. Compound III is condensed with an ethoxypropenoate derivative (IV) in the presence of base such as KOH, NaOH or NaOEt, for 3–12 h to give the aminopyrimidinylthiazole V. Saponification of V in the presence of base such as potassium hydroxide or sodium hydroxide, in a suitable alcoholic solvent such as ethanol, gives the acid VI.

The acid VI can be readily converted to the compounds of this invention via two paths. The treatment of acid VI with a substituted diamine and an appropriate coupling agent, such as dicyclohexylcarbodiimide or carbonyldiimidazole in a suitable solvent such as dimethyl sulfoxide (DMSO), N,N-dimethylformamide (DMF) or methylene chloride at room temperature to 60° C. for 6–72 h gives the amide VIII where Q=NR₃R₄. In a similar manner, treatment of acid VI with a substituted aminoalkanol and an appropriate coupling agent, such as dicyclohexylcarbodiimide or carbonyldiimidazole in a suitable solvent such as dimethyl sulfoxide (DMSO), N,N-dimethylformamide (DMF) or methylene chloride at room temperature to 60° C. for 6–72 hours gives the amide VIII where Q=OH.

Alternatively, acid VI can be treated with a halogenated alkylamine and an appropriate coupling agent, such as dicyclohexylcarbodiimide or carbonyldiimidazole in a suitable solvent such as DMSO, DMF or methylene chloride, at room temperature to 60° C. for 6–72 hours to give the halide derivative VII. Treatment of VII with any appropriate nudeophile, such as a substituted amine or sodium salt of an alcohol, in the presence or absence of a suitable solvent such as DMF, at room temperature to 60° C. for 6–72 hours gives the amide VIII where Q=NR₃R₄ or OR.

The amide VIII, where Q=NH₂, can be converted to a substituted amidine (Q=N=CH—NMe₂) by treatment with dimethylformamide dimethylacetal. Likewise the amide VIII, where Q=NH₂, can be converted to a guanidine by treatment with 1-guanyl-3,5-dimethylpyrazole nitrate in the presence of excess triethylamine.

EXAMPLES

The invention will now be illustrated by examples. The examples are not intended to be limiting of the scope of the present invention. In conjunction with the detailed and general description above, the examples provide further understanding of the present invention and outline a process for producing the compounds of the invention.

The following examples represent preferred embodiments of the compounds, compositions, processes and methods of the invention for satisfying the stated objects of the invention.

Melting point determinations were carried out on a Thomas Hoover capillary melting point apparatus and are uncorrected. All compounds had spectra (elemental analysis, IR, $^1$H NMR, MS) consistent with their assigned structures. Nuclear magnetic resonance (NMR) spectra for hydrogen atoms were measured in the indicated solvent with tetramethylsilane (TMS) as the internal standard on a GE QE-300 spectrometer. The values are expressed in parts per million downfield from TMS. Elemental analyses were determined on a Perkin Elmer 2400 spectrometer and are expressed in percentage by weight of each element per total molecular weight and such found values are reported in the tables and are consistent with the assigned structures. The mass spectra (MS) were determined on a Finnigan Mat 8230 or a Finnigan Mat INCOS 50, single stage, quadrupole using desorption chemical ionization techniques. All column chromatography was run using Silica Gel 60, 230–400 mesh and any appropriate commercially available solvent. Unless otherwise noted, the materials used in the examples are obtained from readily available commercial suppliers or synthesized by standard methods known to anyone skilled in the art of chemical synthesis. The substituent groups, which vary between examples are assumed to be hydrogen unless otherwise noted.

Example Intermediate 1(Int. 1)

2-Amidino-4-(3-trifluoromethylphenyl)thiazole Hydrobromide

N-Amidinothiourea (0.663 g, 5.62 mM) was added to a solution of 3-(trifluoromethyl)phenacylbromide (1.5 g, 5.62 mM) in EtOH (10 mL) and the reaction mixture was heated at reflux for 3 hours (h). The mixture was concentrated in vacuo to one half volume and the resulting solid precipitate was isolated. This solid was washed with EtOh and dried in vacuo to give the title compound as a solid: melting point (mp) 219°–221° C.;

[1] H NMR (DMSO $d_6$): δ 8.28 (m, 5H), 8.07 (s, 1H), 7.71 (m, 2H); MS: 287 (MH$^+$).

The following general procedure was used in the synthesis of the compounds listed in Table 1:

N-Amidinothiourea (1 Molar Equivalent) was added to a solution of an appropriately substituted bromoketone derivative II (1 Molar Equivalent) in a suitable solvent and the reaction mixture was heated at reflux for 3–12 h. The mixture was concentrated in vacuo to one half volume and the resulting solid precipitate was isolated. This solid was washed with an appropriate solvent and dried in vacuo to give the desired compound III as the hydrobromide salt.

TABLE 1

| Intermediate | R | R$_2$ | mp, °C. |
|---|---|---|---|
| Int. 2 | Ph | H | 208–209 |
| Int. 3 | 3-ClPh | H | 223–224 |
| Int. 4 | 4-CH$_3$Ph | H | 283–286 |
| Int. 5 | 4-ClPh | H | 279–281 |
| Int. 6 | Ph | Et | 175–177 |
| Int. 7 | Ph | Me | 183–185 |

Example Int. 8

2-(2-Amino-5-carboethoxy-6-methylpyrimidin-2-yl)-4-(3-trifluoromethylphenyl)thiazole Sodium (1.25 g, 52.4 mM) was added to EtOH (10 mL) and the resulting mixture was stirred at room temperature for 30 minutes (min). 2-Amidino-4-(3-trifluoromethylphenyl)thiazole (15 g, 52.4 mM) was added to the reaction mixture followed by ethoxypropenoate derivative IV (R$_1$=CH$_3$:9.75 g, 52.4 mM) and the resulting mixture was heated to reflux for 3 h. The mixture was cooled to room temperature. The resulting solid precipitate was washed with portions of EtOH followed by ether and dried to give the title compound as a solid: mp 227°–229° C.; MS: 463 (MH$^+$).

Anal Calc'd for C$_{18}$H$_{15}$F$_3$N$_4$O$_2$S: C, 52.94; H, 3.70; N,13.72 Found: C, 52.46; H, 3.42; N,13.61

The following general procedure was used in the synthesis of the compounds listed in Table 2:

Sodium (52.4 mM) was added to EtOH (10 mL) and the resulting mixture was stirred at room temperature for 30–60 min. An appropriately substituted guanidinothiazole derivative III (52.4 mM) was add to the reaction mixture followed by ethoxypropenoate derivative IV (1 Molar Equivalent) and the resulting mixture was heated to reflux for 3–12 h. The mixture was cooled to room temperature. The resulting solid precipitate was washed with a suitable solvent and dried. The solid was used as isolated or purified by any of the standard techniques which include column chromatography and recrystallization to give the desired derivative V as a solid.

TABLE 2

| Intermediate | R | R$_1$ | R$_2$ | mp, °C. |
|---|---|---|---|---|
| Int. 9 | 3-ClPh | CF$_3$ | H | 236–38 |
| Int. 10 | 3-CF$_3$Ph | Ph | H | 222–224 |
| Int. 11 | Ph | CF$_3$ | CH$_3$CH$_2$ | 208–210 |
| Int. 12 | Ph | CF$_3$ | CH$_3$ | 234–236 |

Example Int. 13

4(3-Chlorophenyl)-2-[5-carboxy-4-trifluoromethyl-pyrimidin-2-yl)amino]thiazole 0.25 hydrate To a mixture of the thiazole aminopyrimidine ester V (R=3-ClPh, R$_1$=CF$_3$: 15.24 g, 35.6 mM) in i-PrOH (500 mL) was added KOH (3.98 g, 71.2 mM). The resulting solution was stirred at reflux for 16 h, cooled to room temperature and concentrated in vacuo. The residual semi-solid was dissolved in water, acidified with concentrated HCl and filtered to give a solid. This solid was washed with water and ether to give the title compound as a solid: mp 305°–307° C.

Anal Calc'd for C$_{15}$H$_8$ClF$_3$N$_4$O$_2$S.0.25H$_2$O: C, 44.45; H, 2.11; N, 13.82 Found: C, 44.46; H, 1.82; N, 13.51

The following general procedure was used to synthesize the compounds listed in the Table 3:

To a mixture of an appropriate thiazole aminopyrimidine ester V (35.6 mM) in a suitable solvent (500 mL) was added an appropriate base (71.2 mM). The resulting solution was stirred at reflux for 1–16 h, cooled to room temperature and concentrated in vacuo. The residual semi-solid was dissolved in water, addified with concentrated HCl and filtered to give a solid. The solid was purified by recrystallization from a suitable organic solvent to give the desired acid derivative VI, or used without further purification. If a solid did not form upon addification, the reaction mixture was extracted with successive portions of a suitable solvent. The organic extracts were dried (MgSO$_4$), concentrated in vacuo and recrystallized to give the desired add VI.

TABLE 3

| Intermediate | R | R$_1$ | R$_2$ | mp, °C. |
|---|---|---|---|---|
| Int. 14 | Ph | CF$_3$ | Et | 223–225 |
| Int. 15 | 3-CH$_3$Ph | Ph | H | 294–296 |

Example 1 (Cmpd 1)

4-(4-Methoxyphenyl)-2-[N-[4-[3-(N,N-diethylamino)propylcarbamoyl]-5-trifluoromethyl-2-pyrimidinyl]amino]thiazole Hemihydrate A mixture of the acid derivative VI (R=4-CH$_3$OPh, R$_1$=CF$_3$: 1.0 g, 2.5 mM) and carbonyldiimidazole (0.6 g, 3.8 mM) in DMF (15 mL) was stirred at room temperature for 1 h. 1,1-Diethylaminopropylamine (2.1 mL, 12.5 mM) was added to the mixture and the reaction was stirred overnight. The resulting mixture was poured into water (150 mL) and a precipitate was collected. The crude solid was recrystallized from MeOH to give the title compound as a solid: mp 265°–267° C.; MS: 509 (MH$^+$).

Anal. Calc'd for $C_{23}H_{27}F_3N_6O_2S \cdot 0.5\ H_2O$: C, 53.37; H,5.45; N,16.24 Found: C, 53.34; H,5.12; N,16.03

The following general procedure was used in the preparation of the compounds listed in Table 4:

A mixture of the acid derivative VI (1 Molar Equivalent) and carbonyldiimidazole (1.52 Molar Equivalents) in a suitable solvent (6 mL) was stirred at room temperature for 1–4 h. An appropriately substituted alkyldiamine or amino alkanol (3–6 Molar Equivalents) was added to the mixture and the reaction was stirred overnight. The resulting mixture was poured into water and a precipitate was collected. If a precipitate does not form, then the mixture is extracted into an organic solvent such as ethyl acetate or methylene chloride. The organic extracts were dried (MgSO$_4$) and concentrated in vacuo. The crude product was then purified by any of the standard methods which include column chromatography and recrystallization to give the desired compound VIII as a solid. Likewise, treatment of the solid with an acid such as hydrochloric acid, hydrobromic acid, oxalic acid, lactic acid, citric acid or succinic acid in a solvent such as methanol, acetone or diethyl ether provided the corresponding salt.

TABLE 4

| Cmpd | R | R$_1$ | A—NR$_3$R$_4$ | mp, °C. |
|---|---|---|---|---|
| 2 | 4-CH$_3$Ph | CF$_3$ | (CH$_2$)$_3$NEt$_2$ | 289–291 |
| 3 | 3-CF$_3$Ph | CF$_3$ | (CH$_2$)$_3$imidazole | 245–250 |
| 4 | 3-CF$_3$Ph | CF$_3$ | (CH$_2$)$_3$NH$_2$ | 216–218 |
| 5 | 4-CH$_3$OPh | CF$_3$ | (CH$_2$)$_3$NMe$_2$ | 260–262 |

Example 6

2-[5-[3-(Cyclohexylamino)propylcarbamoyl)-4-trifluoromethylpyrimidin-2-yl]amino]-4-(3-trifluoromethylphenyl)thiazole (Cmpd 6)

A mixture of the acid derivative VI (R=3-CF$_3$Ph, R$_1$=CF$_3$: 2.0 g, 4.6 mM) and carbonyldiimidazole (0.74 g, 4.6 mM) in DMF (25 mL) was stirred at room temperature for 30 min. 3-Bromopropylamine hydrobromide (2.0 g, 9.2 mM) was added and the resulting amber solution was stirred at room temperature for 2 h, poured into water (100 mL) and stirred overnight at room temperature. The resulting precipitate was collected by filtration and dried to give the bromo derivative VII (A=(CH2)$_3$, Q=Br) as a solid: mp 236°–238° C.; MS: 516 (MH$^+$). Cyclohexylamine (2 mL, 1.1 mM) was added to a solution of the bromo derivative VII (R=3-CF$_3$Ph, R$_1$=CF$_3$, A=(CH2)$_3$, Q=Br: 600 mg, 1.1 mM) in DMF (25 mL) and the reaction mixture was stirred overnight at room temperature. The resulting mixture was concentrated in vacuo to a volume of 5 mL and purified by column chromatography on silica gel using 5% Et$_3$N: MeOH/CH$_2$Cl$_2$ (1:9) to give the title compound as a solid: mp 250°–252° C.; MS: 573 (MH$^+$).

Anal Calc'd for $C_{25}H_{26}F_6N_6OS$: C, 52.44; H, 4.58; N,14.68 Found: C, 51.41; H, 4.51; N,14.67

The following general procedure was used in the synthesis of the compounds contained in Table 5:

A mixture of an appropriate acid derivative VI (1 Molar Equivalent) and carbonyldiimidazole (1.5–2.0 Molar Equivalents) in DMF was stirred at room temperature for 0.5–2 h. 3-Bromopropylamine hydrobromide (2.5–6 Molar Equivalents) was added and the resulting solution was stirred at room temperature for 1–2 h, poured into water and stirred at room temperature. The resulting precipitate was collected by filtration and dried to give the desired bromide VII (A=(CH$_2$)$_3$, Q=Br) as a solid. An appropriately substituted amine (1 Molar Equivalent) was added to a solution of a suitable bromo derivative VII in an appropriate solvent (25 mL) and the reaction mixture was stirred overnight at room temperature. The resulting mixture was concentrated in vacuo and purified by a standard methods, e.g. column chromatography and recrystallization, to give the the desired compound VIII as a solid. Likewise, treatment of the residue with an acid such as hydrochloric acid, hydrobromic acid, oxalic acid, lactic acid, citric acid or succinic acid in a solvent such as methanol, acetone or diethyl ether provided a salt.

TABLE 5

| Cmpd | R | R$_1$ | R$_2$ | A—NR$_3$R$_4$ | mp, °C. |
|---|---|---|---|---|---|
| 7 | 3-CF$_3$Ph | CF$_3$ | H | (CH2)3hexamethylene-imine | 272–274 |
| 8 | 3-CF$_3$Ph | CF$_3$ | H | (CH2)3cyclopentylamine | 305–307 |
| 9 | 3-CF$_3$Ph | CF$_3$ | H | (CH2)3NHBu | 228–230 |
| 10 | 3-CF$_3$Ph | Ph | H | (CH2)3cyclohexylamine | 294–296 |
| 11 | 3-CF$_3$Ph | CF$_3$ | H | (CH2)3pyrrolidinone | 258–260 |
| 12 | 3-CF$_3$Ph | CF$_3$ | H | (CH2)3methylpiperazine | 235–240 |
| 13 | 3-ClPh | CF$_3$ | H | (CH2)3piperidine | 255–257 |
| 14 | 3-ClPh | CF$_3$ | H | (CH2)3hexamethylene-imine | 235–237 |
| 15 | 3-ClPh | CF$_3$ | H | (CH2)3cyclohexylamine | 258–260 |
| 16 | 3-ClPh | CF$_3$ | H | (CH2)3-NHPr | 195–197 |
| 17 | 4-CH$_3$Ph | CF$_3$ | H | (CH$_2$)$_3$NHbutyl | 216–218 |
| 18 | Ph | CF$_3$ | CH$_3$ | (CH2)3cyclohexylamine | 194–196 |

BIOLOGICAL ASSAYS

Platelet Aggregation Inhibition Activity

The percentage of platelet aggregation is calculated as an increase in light transmission of drug treated platelet concentrate vs control treated platelet concentrate. Blood is obtained from drug free, normal donors and placed into tubes containing 0.13M sodium citrate (two sources are routinely used: platelet concentrate obtained from Biological Specialty Corp., Lansdale, Pa. or whole blood obtained from donors). Platelet rich plasma (PRP) is collected by centrifugation of the concentrate or whole blood at 130×g for 15 minutes at 25° C. The PRP (5 mL) is gel filtered through Sepharose 2B (bed volume 50 mL), and the platelet count is adjusted to 2×10⁷ platelets per sample. The following constituents are added to a siliconized cuvette: 250 µL of the concentrated platelet filtrate, 100 µL of Tyrode's buffer (0.14M NaCl, 0.0027M KCl, 0.012M NaHCO$_3$, 0.76 mM Na$_2$HPO$_4$, 0.0055M glucose and 2 mg/mL BSA pH 7.4), 50 µL of 2 mM calcium and test drug (50 mL). Aggregation is monitored in a dual channel Chrono-log Aggregometer for three minutes following the addition of agonist (thrombin 50 µL of 1 unit/mL, or ADP 50 µL of 100 µM). The final assay volume is 500 µL. The reaction takes place at 37° C. The peak aggregation response is calculated as the increase in light transmission units over a three minute period. The difference of the increase in light transmission between control and drug treated platelets is then expressed as a percent of the nondrug treated controls. The percentage of inhibition of platelet aggregation of certain selected compounds at 50 µM is displayed in Table 6.

Fibrinogen Binding

The compounds of the invention as identified above are evaluated for platelet aggregation inhibition activity as indicated by the percentage of non-aggregated platelets which are available for binding in accordance with the following procedure.

$^{125}$I-Fibrinogen binding to activated platelets is a modification of the procedure described by Bennett et al., 1988. Briefly, 40 mL of PRP (obtained from Biological Specialty Corp., Lansdale, Pa.) are centrifuged at 120×g to remove contaminating red cells. Aspirin (50 µM) is added and the PRP is incubated at 37° C. for 20 minutes. The pH of the PRP is adjusted to 6.5 with 3.8% sodium citrate and 0.9 µM of PGE1 is added. Platelets are concentrated by a 300×g centrifugation (10 minutes) and the pellet is resuspended in 4 mL. of Tyrode's buffer. The platelet suspension (4 mL) is gel-filtered through a Sepharose-2B column (50 mL bed volume). The platelet count is adjusted to 1×108 platelets per 200 mL. The binding reaction is performed in polystyrene tubes (final volume 500 mL). Reagents are added in the following order: 80 mL of Tyrode's buffer, 50 mL of CaCl$_2$ (final concentration (f.c.) 0.2 µM) and 50 mL of thrombin (f.c. 0.1 unit/mL). The platelet suspension is then added and the mixture is allowed to incubate at room temperature for 2 minutes. Hirudin (50 mL, f.c. 0.5 unit/mL) is immediately added to prevent the catalytic activity of thrombin. Various concentrations of the compound to be tested (50 mL) with the competing radioligand $^{125}$I-fibrinogen (f.c. of 0.15 µM) are added. The mixture is incubated for 10 minutes at room temperature. To terminate the binding reaction the platelets are sedimented (10,000×g for 3 minutes) through silicone oil (3:1 hi-phenol 550/methyl silicone 200, W. F. Nye, Inc., New Bedford, Mass.), in an Eppendorf centrifuge.

The tips of the centrifuge tubes containing the pelleted platelets are cut off and counted for $^{125}$I-fibrinogen associated with the stimulated platelets. The amount of platelet radioactivity measured in the presence of nonlabeled fibrinogen (4 mg/mL) is considered the nonspecific binding. All samples are repeated in triplicate.

Data are expressed as a percent at concentrations of 30 µM of specifically bound $^{125}$I-fibrinogen to the platelets in Table 6 below. Positive percentages of fibrinogen binding indicates higher activity for inhibiting platelet aggregation since only non-aggregated or free platelets are available for fibrinogen binding. Alternatively, a concentration is provided in lieu of a percentage to indicate the IC$_{50}$ of concentration of compound which provides 50% fibrinogen binding.

TABLE 6

| Cmpd | % Inhibition Platelet Aggregation @ 50 µM | % Inhibition Fibrinogen Binding @ 30 µM |
|---|---|---|
| 1 | 95% | 35% |
| 2 | 75% | 12% |
| 3 | 55% | 4% |
| 4 | 10 µM | 50% |
| 5 | 96% | 47% |
| 6 | 15 µM | 30 µM |
| 7 | 95% | 14% |
| 8 | 85% | 50% |
| 9 | 96% | 3.4 µM |
| 10 | 25% | 15% |
| 11 | 25% | 10% |
| 12 | 90% | 47% |
| 13 | 94% | 16% |
| 14 | 98% | 15% |
| 15 | 14.8 µM | 73% |
| 16 | 96% | 20% |
| 17 | 36% | 43% |
| 18 | 58% | 47% |

The above test results demonstrate the utility of the compounds of the invention for inhibiting platelet aggregation. The scope of the present invention is not limited by the description, examples and suggested uses described herein and modifications can be made without departing from the spirit of the invention. For example, additional medicaments or active components may be used in combination with the compounds of the invention or two or more compounds of the invention may be used in combination in a pharmaceutical composition. Further, the novel compounds of the invention may have other uses in addition to those described herein.

Pharmaceutical compositions containing compounds of the invention may comprise the compound of the present invention and a pharmaceutically acceptable carrier in either solid or liquid form. Solid form preparations include powders, tablets, dispersible granules, capsules, etc. The carrier may also be one or more substances which act as diluents, flavoring agents, solubilizers, lubricants, suspending agents, binders, or tablet disintegrating agents as well as encapsulating materials. Suitable carriers are magnesium carbonate, magnesium stearate, talc, lactose, sugar, peptin, dextrin, starch, methylcellulose, sodium carboxymethylcellulose, and the like. Liquid form preparations include solutions which are suitable for oral or parenteral administration, or suspensions and emulsions suitable for oral administration.

Sterile water solutions of the active component or sterile solutions of the active components in solvents comprising water, ethanol, or propylene glycol are examples of liquid preparations suitable for parenteral administration. Sterile solutions may be prepared by dissolving the active component in the desired solvent system, then passing the resulting solution through a membrane filter to sterilize it, or alternatively, by dissolving the sterile compound in a previously sterilized solvent under sterile conditions. Aqueous solutions for oral administration can be prepared by dissolving the active compound in water and adding suitable flavorants, coloring agents, stabilizers and thickening agents as required. Aqueous suspensions for oral use can be made by dispersing the finely divided active component in water together with a viscous material such as a natural or synthetic gum, methyl cellulose, sodium carboxy methyl cellulose, and other suspending agents known to the pharmaceutical formulation art.

It is especially advantageous to formulate the aforementioned pharmaceutical compositions in unit dosage form for ease of administration and uniformity of dosage. The term "unit dosage form" as used herein refers to physically discrete units suitable as unit dosages, each unit containing a predetermined quantity of active ingredient calculated to produce the desired therapeutic effect in association with the required pharmaceutical carrier.

Various conventional techniques for preparing pharmaceutical compositions including solutions, suspensions, tablets or caplets can be employed, as would be known to those skilled in the art and as is disclosed for example by *Remington's Pharmaceutical Sciences*, Mack Publishing Co., Part 8 Chapters 76-93, "Pharmaceutical Preparations and Their Manufacture", pp. 1409-1677 (1985).

In therapeutic use as inhibitors of platelet aggregation and/or fibrinogen binding, the compounds utilized in the methods of this invention may be administered to a patient either orally or parenterally at dosage levels from about 1-100 mg/kg and preferably about 3-20 mg/kg of body weight per day. The dosages, however, may be varied depending upon the results of specific clinical testing, the requirements of the patient, the weight and age of the patient, the severity of the condition being treated, and the compound being employed. Determination of optimum dosages for a particular situation is within the skill of the art.

Applications of the compounds, compositions, and methods of the present invention for medical or pharmaceutical uses can be accomplished by any clinical, medical, and pharmaceutical methods and techniques as are presently or prospectively known to those skilled in the art. Thus it is intended that the present invention cover any modifications and variations of this invention provided that they come within the scope of the appended claims and their equivalents.

What is claimed is:

1. A compound of the formula:

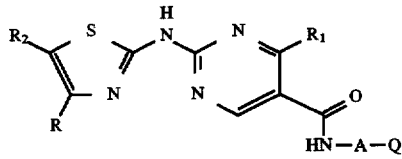

wherein

R and $R_2$ are independently selected from hydrogen, alkyl $(C_1-C_5)$, trifluoromethyl, phenyl, and substituted phenyl, where the phenyl substituents are selected from the group consisting of cyano, nitro, trifluoromethyl, carboxy, amino, carboxamido, tosyl, bromo, chloro, iodo, fluoro, alkyl $(C_1-C_5)$, carboalkoxy $(C_1-C_4)$ and alkoxy $(C_1-C_5)$;

$R_1$ is selected from the group consisting of hydrogen, alkyl $(C_1-C_5)$, trifluoromethyl, phenyl, substituted phenyl and substituted heterocycle wherein the phenyl substituents are selected from the group consisting of cyano, nitro, trifluoromethyl, carboxy, amino, carboxamido, tosyl, bromo, chloro, iodo, fluoro, alkyl $(C_1-C_5)$, carboalkoxy $(C_1-C_4)$ and alkoxy $(C_1-C_5)$ and the heterocycle substituents are selected from hydrogen, alkyl $(C_1-C_5)$, trifluoromethyl, phenyl, or substituted phenyl, where the phenyl substituents are selected from the group consisting of cyano, nitro, trifluoromethyl, carboxy, amino, carboxamido, tosyl, bromo, chloro, iodo, fluoro, alkyl $(C_1-C_5)$, carboalkoxy $(C_1-C_4)$ and alkoxy $(C_1-C_5)$;

A is selected from the group consisting of alkyl $(C_2-C_9)$, branched alkyl $(C_3-C_9)$ or phenyl;

Q is selected from hydroxy, alkoxy $(C_1-C_5)$, halogen or $NR_3R_4$, where $R_3$ and $R_4$ are independently selected from the group consisting of hydrogen, alkyl $(C_1-C_5)$, and cycloalkyl $(C_3-C_8)$, or $NR_3R_4$ is taken together to form a heterocyclic ring selected from the group consisting of piperidine, pyrrolidine, pyrrolidinone, piperidinone, phthalimide and imidazole or $NR_3R_4$ is a guanidine, urea, thiourea, amidine, or substituted amidine wherein the substituents are selected from the group consisting of alkyl $(C_1-C_4)$, hydroxyl and amino; and the pharmaceutically acceptable salts thereof.

2. A compound according to claim 1 of the formula:
4-(4-Methoxyphenyl)-2-[N-[4-[3-(N,N-diethylamino)propylcarbamoyl]-5-trifluoromethyl-2-pyrimidinyl]amino]thiazole; 4-(4-Methylphenyl)-2-[N-[4-[3-(N,N-diethylamino)propylcarbamoyl]-5-trifluoromethyl-2-pyrimidinyl]amino]thiazole; 4-(4-Methoxyphenyl)-2-[N-[4-[3-(N,N-dimethylamino)propylcarbamoyl]-5-trifluoromethyl-2-pyrimidinyl]amino]thiazole.

3. A compound according to claim 1 of the formula:
4-(3-Chlorophenyl)-2-[N-[4-[3-(cyclohexylamino)propylcarbamoyl]-5-trifluoromethyl-2-pyrimidinyl]amino]thiazole.

4. A compound according to claim 1 of the formula:
4-(3-Trifluoromethylphenyl)-2-[N-[4-[3-(amino)propylcarbamoyl]-5-trifluoromethyl-2-pyrimidinyl]amino]thiazole.

5. A method of treating reperfusion thrombosis injury in a patient comprising the step of administering to a patient an amount of a compound of claim 2 effective to inhibit platelet aggegation.

6. A method of treating reperfusion thrombosis injury in a patient comprising the step of administering to patient an amount of a compound of claim 3 effective to inhibit platelet aggegation.

7. A method of treating reperfusion thrombosis injury in a patient comprising the step of administering to a patient an amount of a compound of claim 4 effective to inhibit platelet aggegation.

8. A pharmaceutical composition comprising a compound of claim 2 and a pharmaceutically inert carrier.

9. A pharmaceutical composition comprising the compound of claim 3 and a pharmaceutically inert carrier.

10. A pharmaceutical composition comprising the compound of claim 4 and a phamaceutically inert carrier.

11. A compound according to claim 1 selected from those of the formula:
4-(3-Trifloromethylphenyl)-2-[N-[4-[3-(imidazolyl)propylcarbamoyl]-5-triflurormethyl-2-pyrimidinyl]amino]thiaiole; 4-(3-Trifluoromethylphenyl)-2-[N-[4-[3-(cyclohexylamino)propylcarbamoyl]-5-trifluoromethyl-2-pyrimidinyl]amino]thiazole; 4-(3-Trifluoromethylphenyl)-2-[N-[4-[3-(butylamino)propylcarbamoyl]-5-trifluoromethyl-2-pyrimidinyl]amino]thiazole; and 4-(3-Trifluoromethylphenyl)-2-[N-[4-[3-(propylamino)propylcarbamoyl]-5-trifluoromethyl-2-pyrimidinyl]amino]thiazole.

12. A method of treating reperfusion thrombosis injury in a patient comprising the step of administering to a patient an amount of a compound of claim 1 effective to inhibit platelet aggregation.

13. A pharmaceutical composition comprising a compound of claim 1 and a pharmaceutically inert carrier.

14. A pharmaceutical composition comprising a compound of claim 1 and a pharmaceutically inert carrier.

15. A compound according to claim 1 wherein:

R and $R_2$ are independently selected from hydrogen and substituted phenyl wherein the phenyl substitutents are selected from the group consisting of trifluoromethyl, bromo, chloro, iodo, fluoro, alkyl ($C_1$–$C_5$) and alkoxy ($C_1$–$C_5$);

$R_1$ is alkyl ($C_1$–$C_5$) or trifluoromethyl;

A is alkyl ($C_3$); and

Q is $NR_3R_4$, where $R_3$ and $R_4$ are independently selected from the group consisting of hydrogen, alkyl ($C_1$–$C_5$) and cycloalkyl ($C_3$–$C_8$), or $NR_3R_4$ is taken together to form a heterocyclic ring selected form the group consisting of pyrrolidinone and imidazole.

16. A method of treating reperfusion thrombosis injury in a patient comprising the step of administering to a patient an amount of a compound of claim 15 effective to inhibit platelet aggregation.

17. An intermediate compound according to the formula:

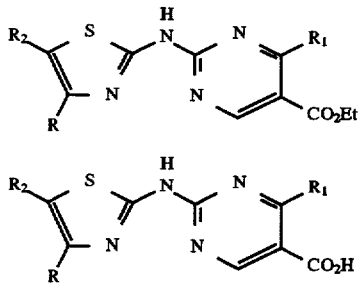

wherein

R and $R_2$ are independently selected from hydrogen, alkyl ($C_1$–$C_5$), trifluoromethyl, phenyl, or substituted phenyl, where the phenyl substituents are selected from the group consisting of cyano, nitro, trifluoromethyl, carboxy, amino, carboxamido, tosyl, bromo, chloro, iodo, fluoro, alkyl ($C_1$–$C_5$), carboalkoxy ($C_1$–$C_4$) and alkoxy ($C_1$–$C_5$);

$R_1$ is selected from the group consisting of hydrogen, alkyl ($C_1$–$C_5$), trifluoromethyl, phenyl, substituted phenyl and substituted heterocycle wherein the phenyl substituents are selected from the group consisting of cyano, nitro, trifluoromethyl, carboxy, amino, carboxamido, tosyl, bromo, chloro, iodo, fluoro, alkyl ($C_1$–$C_5$), carboalkoxy ($C_1$–$C_4$) and alkoxy ($C_1$–$C_5$) and the heterocycle substituents are selected from hydrogen, alkyl ($C_1$–$C_5$), trifluoromethyl, phenyl, or substituted phenyl, where the phenyl substituents are selected from the group consisting of cyano, nitro, trifluoromethyl, carboxy, amino, carboxamido, tosyl, bromo, chloro, iodo, fluoro, alkyl ($C_1$–$C_5$), carboalkoxy ($C_1$–$C_4$) and alkoxy ($C_1$–$C_5$);

and the pharmaceutically acceptable salts thereof.

* * * * *